United States Patent [19]
Chen et al.

[11] Patent Number: 5,443,559
[45] Date of Patent: Aug. 22, 1995

[54] BRUSH-TIP ELECTRODE

[75] Inventors: Yunquan Chen; Charles A. Laszlo; Cecil Hershler, all of Vancouver, Canada

[73] Assignee: The University of British Columbia, Vancouver, B.C., Canada

[21] Appl. No.: 156,732

[22] Filed: Nov. 24, 1993

Related U.S. Application Data

[63] Continuation-in-part of Ser. No. 969,458, Oct. 30, 1992, Pat. No. 5,299,572.

[51] Int. Cl.⁶ ............................................ A61B 5/0492
[52] U.S. Cl. .................................................. 128/639
[58] Field of Search ................... 128/639–644, 128/733; 607/115, 116, 122, 149–151; 15/167.1, 167.3; 51/391, 392

[56] References Cited

U.S. PATENT DOCUMENTS

| Re. 16,869 | 2/1928 | Goldman | 15/167.3 |
|---|---|---|---|
| 3,620,208 | 11/1971 | Higley | 128/2.06 E |
| 3,882,846 | 5/1975 | Fletcher et al. | 128/2.06 E |
| 4,538,612 | 9/1985 | Patrick, Jr. | 128/639 |
| 4,574,814 | 3/1986 | Buffet | 128/786 |
| 4,685,466 | 8/1987 | Rau | 128/639 |
| 4,706,679 | 11/1987 | Schmidt et al. | 128/639 |
| 4,920,968 | 5/1989 | Takase | 128/639 |
| 4,969,468 | 11/1989 | Byers et al. | 128/642 |
| 5,038,787 | 8/1991 | Gevins et al. | 128/644 |

FOREIGN PATENT DOCUMENTS

| 890205 | 2/1944 | France | 15/167.3 |
|---|---|---|---|
| 3025955 | 1/1982 | Germany | |
| 9826 | 11/1909 | United Kingdom | 606/131 |
| 1556749 | 7/1976 | United Kingdom | |
| 1551345 | 3/1990 | U.S.S.R. | |

OTHER PUBLICATIONS

Elden, Harry R., "Biophysical Properties of the Skin", New York: Wiley-Interscience [1971] pp. 513–550.

Reucher et al., "Spatial Filtering of Noninvasive Multielectrode EMG: Part 1-Introduction to Measuring Technique and Applications", IEEE Transactions on Biomedical Engineering, vol. BME-34, No. 2, Feb. 1987.

Masuda et al., "Topographical Map of Innervation Zone Within Single Motor Units Measured with a Grid Surface Electrode", IEEE Transactions on Biomedical Engineering vol. 35, No. 8, Aug. 1988.

Armstrong James et al., "Carbon Fibre Microelectrodes" Journal of Neuroscience Methods 1979, pp. 279–287 FECMBE '93.

*Primary Examiner*—Lee S. Cohen
*Attorney, Agent, or Firm*—Norman M. Cameron

[57] ABSTRACT

An electrode is used the connecting apparatuses to the skin surface of a living body. It includes a tube having an end and a plurality of hard, resilient wires extending outwardly from the end of the tube. The wires have splayed ends in a brush-tip-like arrangement having an end formed by the spaced-apart wires which is multipointed and abrasive.

18 Claims, 3 Drawing Sheets

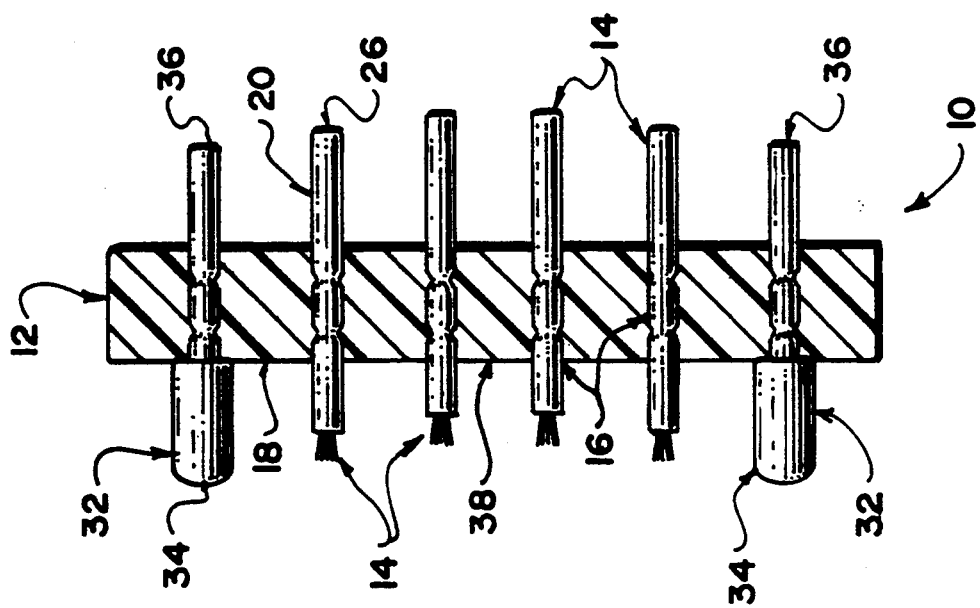
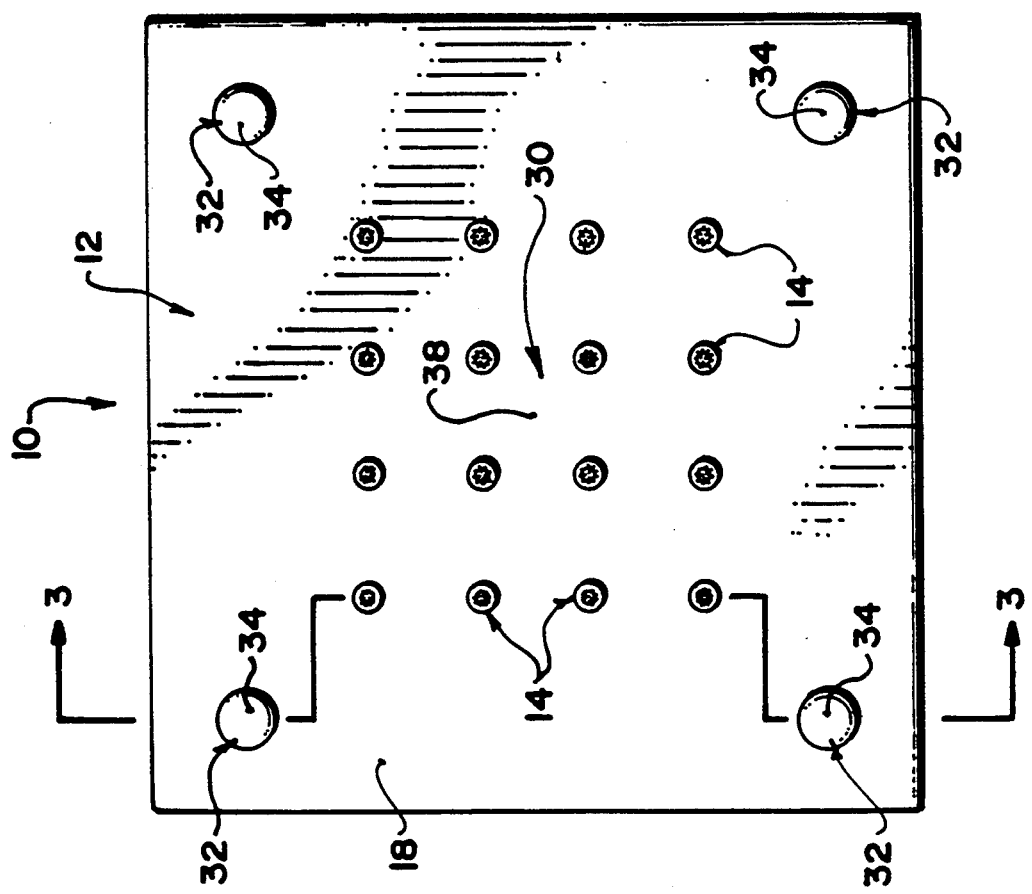

BRUSH-TIP ELECTRODE

BACKGROUND OF THE INVENTION

Related Application

This is a continuation-in-part of U.S. patent app. Ser. No. 07/969,458 filed Oct. 30, 1992.

FIELD OF THE INVENTION

This invention relates to electrodes used in detecting bioelectric signals on a living body, especially for use in detecting electromyographic (EMG) signals from the skin surface of a human body.

DESCRIPTION OF RELATED ART

Electrodes which are conventionally used for the acquisition of EMG signals are either invasive (needle or wire) electrodes which penetrate through the skin into a muscle, or noninvasive surface electrodes which are placed on the skin surface above a muscle. Surface electrodes are preferred for their non-invasive characteristics, but their usefulness is limited. One of the reasons for this is that they pick up concurrent activities of many muscle fibres, yielding complex action potentials which represent summated or averaged activities. Reportedly EMG signals can be obtained selectively from the skin surface, i.e. action potentials of muscle fibres of individual or a small number of motor units can be obtained with appropriate combinations of several surface electrodes. The structural and dynamic properties of a muscle are detectable with the use of groups of similar electrodes appropriately combined. Many basic electrodes are usually combined at fixed distances from each other in one or two dimensions and are conventionally called an electrode array.

The basic electrodes which form tile array must have small contact areas with the skin. Pin electrodes with flat tips have been used in the past in the construction of arrays. However such electrodes have not been very successful because the skin-electrode impedance is too high. Pin electrodes with sharp tips have also been used to investigate the skin electrode impedance with different penetrating depths of the needle point into the skin. The results indicate that the deeper the penetrating depth, the lower the skin-electrode impedance.

U.S. Pat. No. 4,685,466 discloses a quasi-invasive, needle-like electrode which penetrates into the upper, most largely cast-off cell layers of the horny skin to reduce the skin electrode impedance in a very small contact area. Since the contact area between the electrode and the skin is so small, a minimum depth of penetration must be achieved by the electrode in order to reduce the skin-electrode impedance to an acceptable level. On the other hand, the depth must be limited to the thickness of the layer of the stratum corneum of skin (from less than 50 to over 350 micrometers on human skin) in order to keep the electrode non-invasive. However it is difficult or at least inconvenient to determine and control the depth of the penetration of such an electrode in practice, especially when the electrode is pan of an array and when motion occurs on the skin or in the muscle. In addition, regular electrolytic treatment is also necessary for electrodes of such small contact area to reduce the impedance of the electrodes themselves.

An example of an electrode array is found in U.S. Pat. No. 4,969,468 to Byers et al. The electrode array includes a base and a plurality of electrically conductive protuberances extending substantially perpendicular to and from the support surface of the base in a two dimensional array. Each of the protuberances has a tip for electrically contacting the tissue.

The prior an discloses various ways to improve types of biological electrodes other than those for electrode arrays suitable for EMG electrodes. Such other types typically have much larger skin contact areas (usually greater than 5 mm$^2$). An example is found in U.S. Pat. No. 3,882,846 to Fletcher. The electrode system includes an insulated electrode and an impedance transformer. Another example is found in U.S. Pat. No. 4,706,679 to Schmidt. This electrode comprises bundles of soft, silver wires held by a conductive tube with a flat tip. These however are large area electrodes which are intended to be used individually and not in an array. The wires are thick (127 $\mu$m in diameter) and are tightly packed with an outer end forming a planar surface. The contact area is relatively large (about 4 mm$^2$). U.S. Pat. No. 5,038,782 to Gevins discloses an EEG electrode with separate, relatively large diameter fingers (at least 2.45 mm). The tips are smooth, non-pointed, and non-abrasive. Like the Schmidt electrode it is not well suited for use with acquisitions of EMG signals and similar purposes which require small contact areas and are capable of penetrating the outer layer of skin.

SUMMARY OF THE INVENTION

It is an object of the present invention to provide an electrode which has a small area of skin contact, yet has acceptable skin-electrode impedance without the need of determining and controlling the depth of penetration of the electrode into the skin.

It is a further object of tile invention to provide an improved electrode which is suitable for detecting low level bio-electric signals, especially EMG signals from the skin surface of a living body.

In accordance with these objects, there is provided an electrode used for connecting apparatuses to the skin surface of a living body. The electrode includes a tube having an end and a plurality of hard, resilient wires extending outwardly from the end of the tube. The wires have splayed ends in a brush-tip-like arrangement and having an end formed by the spaced-apart wires which is multi-pointed and abrasive.

Preferably the resilient wires are of stainless steel or tungsten for example.

BRIEF DESCRIPTION OF THE DRAWINGS

FIG. 2 is a bottom plan view of an array of tile electrodes of FIG. 1;

FIG. 3 is a sectional view of tile base and electrodes of the array of FIG. 2 taken along line 3—3;

DESCRIPTION OF THE PREFERRED EMBODIMENTS

Figure 1:
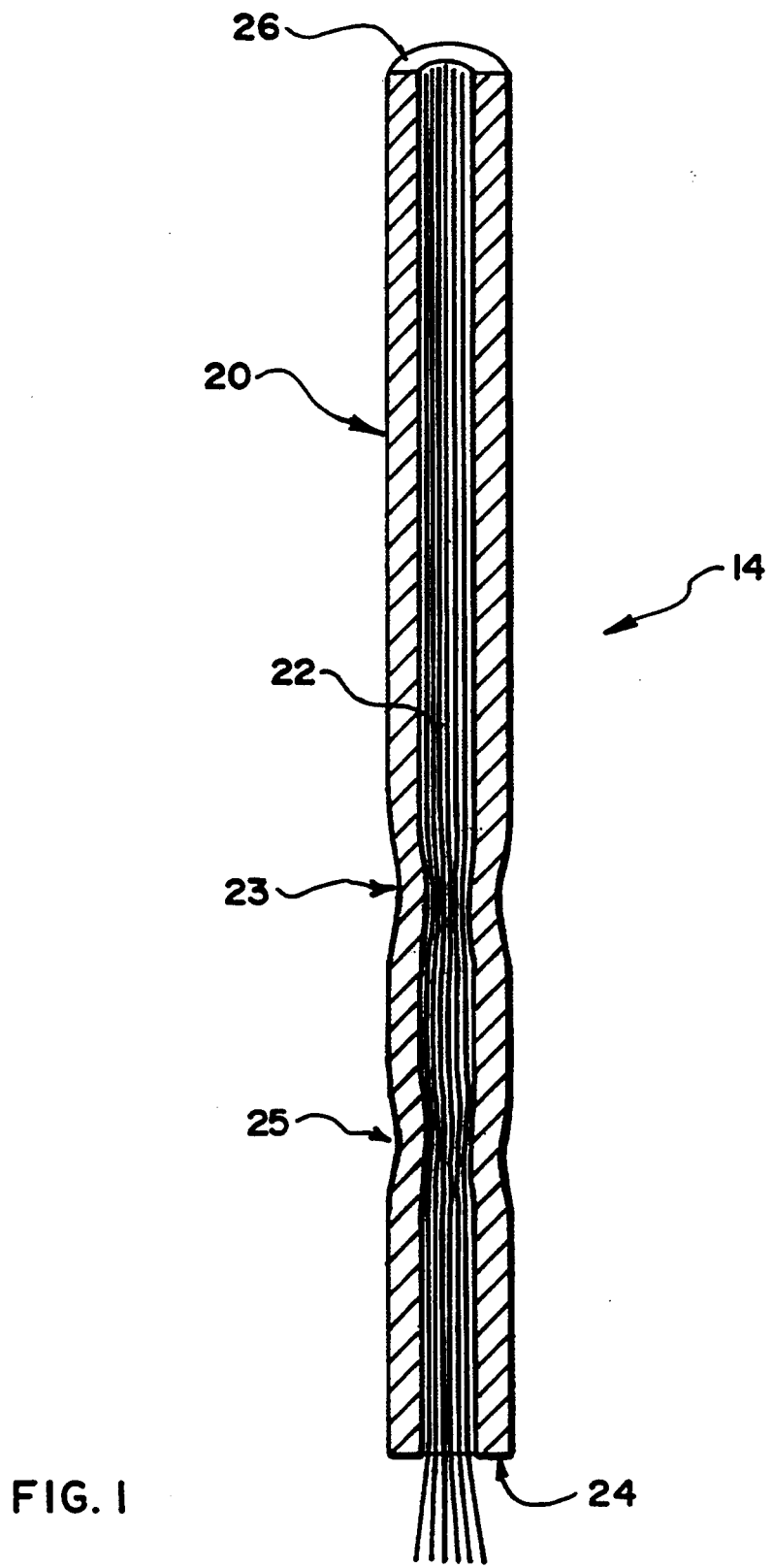
FIG. 1 is a side sectional view of a brush-tip electrode according to an embodiment of the invention.
Figure 5:
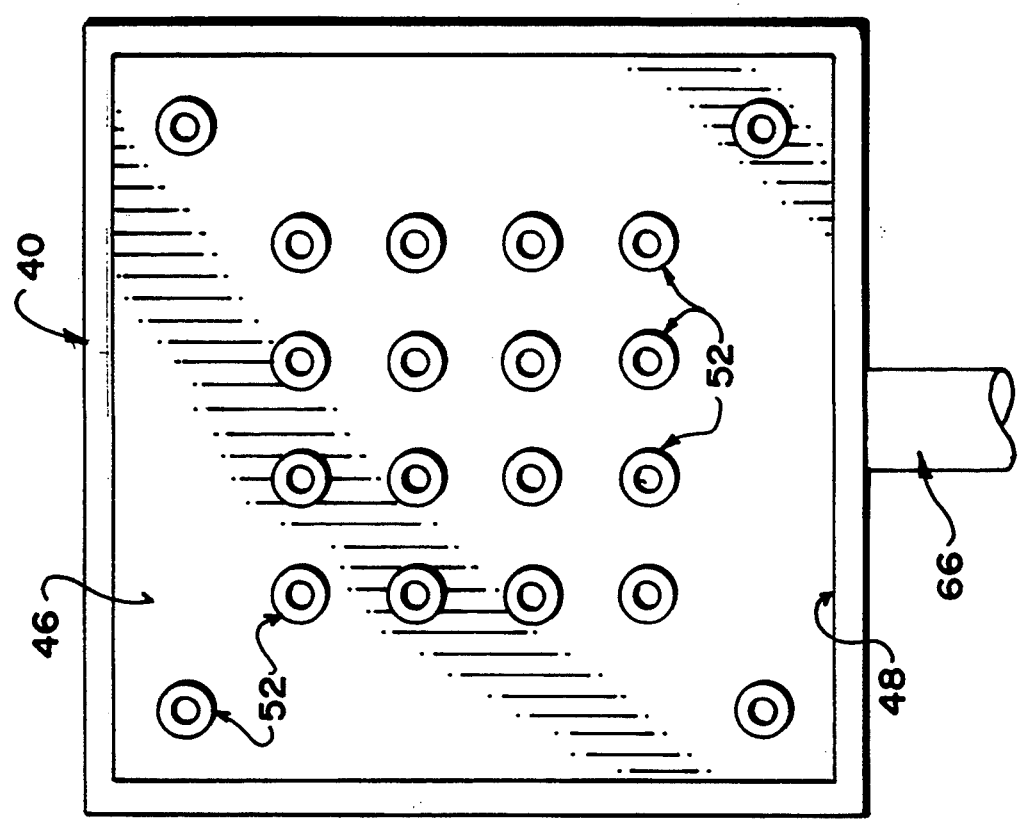
FIG. 5 is a bottom plan view of the case shown in FIG. 4.
Figure 4:
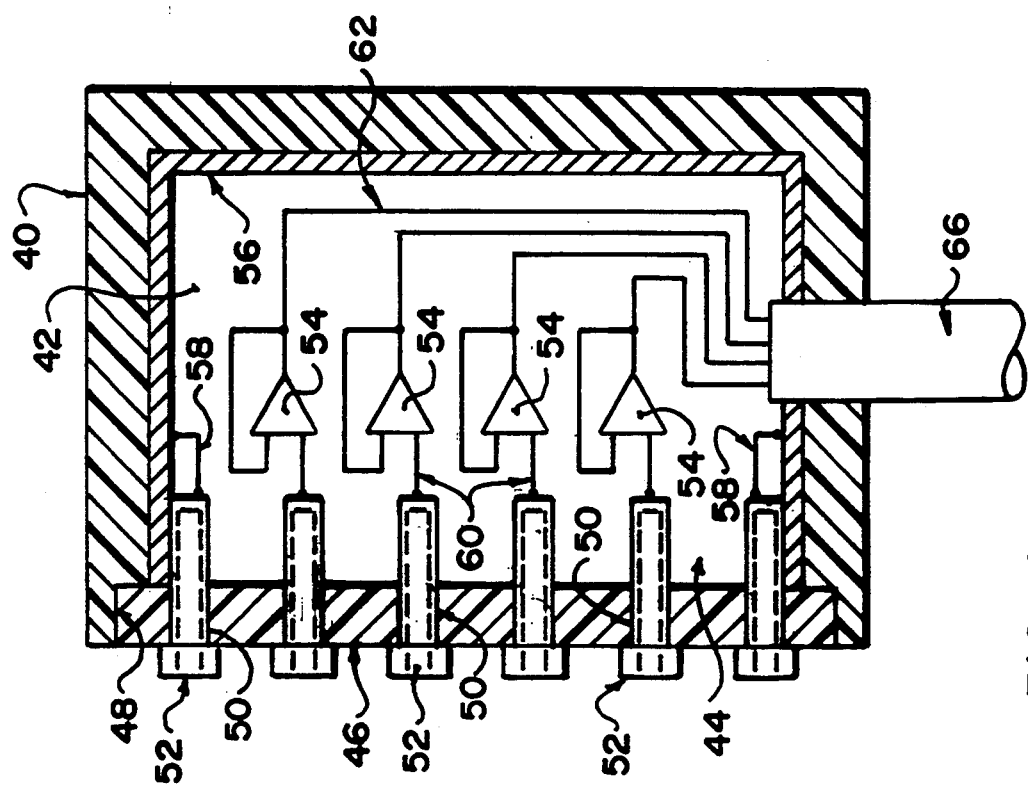
FIG. 4 is a sectional view of the case for the array of FIG. 2 and internal components taken along line 3—3 of FIG. 2.

Referring to FIG. 2–5, an electrode array 10 includes an insulating mount 12 having a plurality of brush-tip electrodes 14 extending through apertures 16 in the mount. The number of electrodes in the array is at least two and preferably between three and thirty-two. There are sixteen in this embodiment. The array is preferably less than 10 cm.×10 cm. in size, preferably less than 5 cm.×5 cm. and most preferably less than 1 cm.×1 cm.

In this particular example the mount 12 is rectangular and is made of a suitable insulator such as plastic. The apertures 16 extend through the mount perpendicular to its bottom surface 18. Thus the brush tip electrodes extend perpendicularly outwards from the bottom surface 18 and are parallel to each other.

As seen in better detail in FIG. 1, each brush tip electrode 14 comprises a tube 20 about 0.5 mm in diameter in this example. A medical injection needle cut to a length of 10 mm was used. The tube produced has an inside diameter about 0.25 mm. Other hard elastic metal tubes could be substituted. A plurality of thin but hard and resilient wires 22 extend through the tube and outwardly from its bottom 24. There should be at least 10 wires, preferably 20-50. Thirty tungsten wires were used in this example, tungsten being preferred for its hardness and corrosion resistance in the presence of salt. High hardness stainless steel is a less expensive alternative. Each wire should have a diameter less than 100 $\mu m$, preferably 20-80 $\mu mm$. In this example the diameter is about 38 $\mu m$. Thus the bunch of wires has a diameter of 0.25 mm in this example which is equal to the inside diameter of the tube. The diameter of the electrode should be in any case less than 2.54 mm, preferably less than 1 mm.

The fine wires are held firmly by crimping the tube at locations 23 and 25 which are about 2 mm apart. The wires are cut even with top end 26 of the tube and project 0.5-2.5 mm from the bottom 24 of the tube, preferably 0.7-1.5 mm and most preferably 1.0 mm as in this example. The wires are slightly splayed below the bottom of the tube, forming a tiny brush tip 27 and leaving room for individual wires to bend a bit within the elastic deformation range of the wires. This allows the lengths of the wires to adjust to fit a skin surface which is rough from a microscopic point of view. The approximate area of end 29 of the brush tip is 0.05 to 0.07 mm$^2$. The end 29 is seen to be formed by the ends of the individual wires 22 and is therefore rough, multipointed and abrasive.

As seen in FIG. 2, the brush-tip electrodes 14 in this embodiment are arranged in a rectangular grid about the central area 30 of the insulating mount 12.

They are spaced-apart, preferably less than 10 mm. and more preferably 2-5 mm. In this example they are 2.54 mm. apart.

There is a plurality of shielding electrodes 32, four in this example, extending from the bottom 18 of the insulating mount which are spaced-apart about the central area and the brush-tip electrodes. As seen best in FIG. 3, each of the shielding electrodes 32 has a bladelike protrusion 34 extending outwardly from the mount and a top end 36 which forms a male electrical connector similar to tops 26 of the brush-tip electrodes.

Mount 12 has a center 38 shown in FIG. 2 and 3. It may be observed in FIG. 3 that the brush-tip electrodes 14 extend further outwards from bottom 18 of the mount with increasing distance from center 38 of the mount. Shielding electrodes 32 are located further outwards and extend even further from the mount. Thus, as seen best in FIG. 3, the shielding electrodes and brush-tip electrodes form a concave shape which better conforms to the living body to be fitted with the electrode array 10.

The larger shielding electrodes 32 are used for two purposes. First, they support the brush tip electrodes, preventing possible high pressure between the skin and these electrodes when the array is applied to the skin surface. Second, they connect the shielding case of the electrode array to the skin surface as described below.

The electrode array 10 also includes a case 40 which is generally box-shaped with an interior cavity 42 and an open bottom 44 provided with a cover 46. The cover fits within a rectangular recess 48 extending about the open bottom 44. The cover 46 has a plurality of apertures 50, each of which is fitted with a female electrical connector 52. There is one female electrical connector 52 positioned to correspond to each of the brush-tip electrodes 14 and shielding electrodes 32 shown in FIG. 2 and 3. In use, the tops 26 and 36 of electrodes 14 and 32 respectively fit within the female electrical connectors 52.

A plurality of signal buffers 54 are located within cavity 42. A brush-tip electrode has an acceptable skin-electrode resistance level for a FET input amplifier to release its input bias current through the electrode, so a simple voltage follower using an operational amplifier is used as a signal buffer in this embodiment. Because no resistors, capacitors or the like are required, a large number of signal buffers can be built into the relatively small cavity 42. Building the signal buffers into the cavity of the case 40 results in a very simple and small sized electrode array.

There is an electrically conductive shielding 56 which extends about the cavity 42 inside the case 40. A suitable metal such as copper or aluminum is suitable. Conductors 58 connect the shielding to the outer female connectors 52 which connect to the shielding electrodes 32. Thus the shielding is not connected to ground, but rather to the skin surface of the living body to which the electrode array is fitted. Such skin-surface equipotential (SSEP) shielding induces less degradation to the input impedance of the signal buffers than grounded shielding. This is due to less distributed capacitive coupling between the electrode leads and the SSEP shielding. The SSEP shielding is achieved by connecting the shielding to and only to the skin surface through the female connectors and the shielding electrodes. Thus the case 40 is passively driven by the skin-surface potential. It is also possible to use a voltage follower between the skin surface and the shielding case, creating an active SSEP driver for the shielding conductor case.

Each of the signal buffers 54 is connected to one of the female connectors 52 by means of a conductor 60. As discussed, each of the inner female connectors 52 is connected to one of the brush-tip electrodes 14. Conductors 62 connect the buffers to a cable 66 extending to the electrical equipment.

The assembly comprising tile electrodes 14 and 32 and the mount 12 is removably connected to the rest of the electrode array 10 by means of the male top ends 26 and 36 of the electrodes fitting within the female connectors 52. This allows the electrodes to be separated from the signal buffers for easy replacement of damaged electrodes and to allow for various configurations and shapes of electrodes to fit different skin surfaces.

Compared to a similar diameter pin electrode with a flat tip, a brush-tip electrode is as easy to deal with when applied to the skin as the flat tip electrode, but has a much lower skinelectrode impedance. A brush-tip electrode of a size suitable for forming the electrode array has the same order of skin-electrode impedance as a sharp tip pin electrode which is not convenient to use in practice. Furthermore, the brush-tip electrode has a much flatter skinelectrode impedance frequency response compared to the sharp tip pin electrode and does not require electrolytic treatment for the electrodes.

Due to the excellent performance of the brush-tip electrodes, the effective SSEP shielding and the direct connection of the electrode array to the electronics, higher quality recordings of bio-electric signals can be obtained repetitively and reliably.

When compared to the electrode of U.S. Pat. No. 4,706,679 to Schmidt, the electrodes have two different primary purposes. The Schmidt electrode is an EEG electrode while the present one is primarily intended as a multi-channel EMG electrode. As discussed above, the size of the electrodes is quite different and the Schmidt electrode cannot simply be downscaled. The use of thin, hard wires of hard stainless steel or tungsten which are slightly splayed gives the improved skin-electrode contact required for an array of EMG electrodes. The fine wires provide better contact with the living layer of skin under the outermost dead layer which contributes most of the skin impedance. Schmidt used thick, soft silver wire bunched together with a planar tip to avoid hurting the patient. This problem does not arise where an array of electrodes are used with much harder, but much thinner wire in the case of the present invention. The pressure of the array on the patient is distributed amongst the plurality of electrodes used (20 in the illustrated example).

It should be understood however that tile electrodes 14 may be useful for other purposes besides the illustrated application as part of an array of electrodes for EMG signals.

It will be understood by someone skilled in tile an that many of the details given above are by way of example only and are not intended to limit the scope of the invention which is to be interpreted with reference to the following claims.

What is claimed is:

1. An electrode used for connecting apparatuses to the skin surface of a living body, the electrode comprising:
    a conductive tube having an end; and
    a plurality of hard, resilient, conductive wires extending outwardly from the end of the tube, the wires having spaced-apart ends and being splayed in a brush-tip-like arrangement having an end formed by the spaced-apart ends of the wires, the end of the arrangement being multipointed and abrasive.

2. An electrode as claimed in claim 1, wherein there are at least 10 said wires.

3. An electrode as claimed in claim 1, wherein there are between 20 and 50 said wires.

4. An electrode as claimed in claim 1, wherein there are 30 said wires.

5. An electrode as claimed in claim 1, wherein the wires are elastic so as to conform to a rough skin surface.

6. An electrode as claimed in claim 1, wherein the wires are of tungsten.

7. An electrode as claimed in claim 1, wherein the wires are of stainless steel.

8. An electrode as claimed in claim 1, wherein each said wire has a diameter less than 100 $\mu$m.

9. An electrode as claimed in claim 1, wherein each said wire has a diameter of between 20 and 80 $\mu$m.

10. An electrode as claimed in claim 1, wherein each of the wires is 38 $\mu$m in diameter.

11. An electrode as claimed in claim 1, wherein the brush-tip-like arrangement has a diameter less than 2.54 mm.

12. An electrode as claimed in claim 1, wherein the brush-tip-like arrangement has a diameter less than 1 mm.

13. An electrode as claimed in claim 1, wherein the wires extend 0.5 mm to 2.55 mm. from the tube.

14. An electrode as claimed in claim 13, wherein the wires extend 0.7 to 1.5 mm. from the tube.

15. An electrode as claimed in claim 14, wherein the wires extend 1 mm. from the tube.

16. An electrode as claimed in claim 14, wherein the tube is a length of medical injection needle.

17. An electrode for connecting apparatuses to the skin surface of a living body, the electrode comprising:
    a conductive tube having an end; and
    at least 10 hard, resilient, conductive wires extending 0.5 mm to 2.5 mm from the tube, the wires each being less than 100 $\mu$m in diameter, the wires having ends and being splayed to form a brush-tip-like arrangement less than 2.54 mm. in diameter, the ends of the wires being spaced-apart and forming a multi-pointed, abrasive end on the electrode.

18. An electrode as claimed in claim 17, including between 20 and 50 said wires, the wires being of tungsten and each having a diameter of 20 to 80 $\mu$m and the brush-tip-like arrangement having a diameter less than 1 mm. and extending 0.7 to 1.5 mm. from the tube.

* * * * *